United States Patent [19]

Andrews

[11] Patent Number: 4,514,359

[45] Date of Patent: Apr. 30, 1985

[54] NONPRECIOUS DENTAL ALLOY

[75] Inventor: Henry L. Andrews, Old Saybrook, Conn.

[73] Assignee: Austenal International, Inc., Chicago, Ill.

[21] Appl. No.: 480,426

[22] Filed: Mar. 30, 1983

[51] Int. Cl.$^3$ .............................................. C22C 19/07
[52] U.S. Cl. .................................... 420/436; 420/435; 433/207
[58] Field of Search ................ 420/436, 435; 148/425; 433/207, 222, 200

[56] References Cited

U.S. PATENT DOCUMENTS

| | | | |
|---|---|---|---|
| 3,134,670 | 5/1964 | Prosen | 75/171 |
| 3,907,555 | 9/1975 | Dudek et al. | 75/171 |
| 3,948,653 | 4/1976 | Tesk et al. | 75/171 |
| 4,038,074 | 7/1977 | Davitz | 75/171 |
| 4,053,308 | 10/1977 | Tesk et al. | 75/171 |
| 4,229,215 | 10/1980 | Prosen | 75/134 C |
| 4,255,190 | 3/1981 | Prosen | 75/134 C |
| 4,382,909 | 5/1983 | Zwingmann | 420/436 |
| 4,459,262 | 7/1984 | Kalmár | 420/436 |

FOREIGN PATENT DOCUMENTS

| | | | |
|---|---|---|---|
| 105755 | 3/1978 | Japan | 420/436 |
| 53-31520 | 3/1978 | Japan | |

Primary Examiner—L. Dewayne Rutledge
Assistant Examiner—Debbie Yee
Attorney, Agent, or Firm—Robert E. Wagner; Alan L. Barry

[57] ABSTRACT

A nonprecious alloy for porcelain-bonded dental restorations consists essentially of, in approximate percentage by weight, 25-30 chromium, 5-7 molybdenum, 0-1.0 each manganese and silicon, 0-0.3 carbon and 0-4 each gallium and indium, balance cobalt, these constituents accounting for at least 99.5 percent of the alloy, the sum of the manganese and silicon being at least about 0.5 percent and the sum of the gallium and indium being at least about 1.25 percent.

2 Claims, No Drawings

NONPRECIOUS DENTAL ALLOY

BACKGROUND OF THE INVENTION

This invention concerns a nonprecious, nonnickel, casting alloy for porcelain-bonded dental restorations.

A metal or alloy intended for dental restorations such as crowns and bridges must be strong, tough, biocompatible and resistant to tarnish, oxidation and corrosion in addition to being capable of forming precise castings. When the alloy is to be bonded to porcelain, it must additionally adhere well to the porcelain and having a coefficient of thermal expansion comparable to that of the porcelain.

The noble metals were used in preparing early dental restorations, since they are very effective for this purpose. Because of the high cost involved with such use, however, replacement of noble by nonprecious metals has constantly been sought. This search has focused primarily on nickel and cobalt based alloys, with numerous compositions being proposed.

Among the elements added to these nonprecious alloy compositions are gallium and indium, such additions being disclosed, for example, in U.S. Pat. Nos. 3,134,670, 3,907,555, 3,948,653, 4,038,074, 4,053,308, 4,229,215 and 4,255,190, and in Japanese Disclosed Application No. 31520/1978. These alloys, however, are in general rather complex, often containing ten or more elements. Also, the biocompatibility of nickel in dental applications has recently been questioned.

It is therefore a primary objective of the present invention to provide a nonprecious, nonnickel, dental casting alloy for porcelain bonding which is comparatively simple in nature and easy to prepare.

SUMMARY OF THE INVENTION

The dental alloy of the present invention consists essentially of the following constituents in approximate percentage by weight:
 chromium—25–30
 molybdenum—5–7
 manganese—0–1.0
 silicon—0–1.0
 carbon—0–0.3
 gallium—0–4
 indium—0–4
 cobalt—balance
said constituents accounting for at least 99.5 weight percent of the alloy, the sum of the manganese and the silicon being at least about 0.5 percent, and the sum of the gallium and indium being at least about 1.25 percent.

In preferred embodiments, the gallium or indium content is from about 1.5 to 3 percent, with the gallium and the indium being present in the alloy either alone or in combination. Such alloys preferably contain about 28 percent chromium and about 6 percent molybdenum. Especially preferred is such an alloy containing about 28 percent chromium, about 6 percent molybdenum, about 0.5 percent manganese, about 0.6 percent silicon, about 0.05 percent carbon and about 1.7 percent indium.

DETAILED DESCRIPTION OF THE INVENTION

The instant alloy composition is predominantly of cobalt, chromium and molybdenum with minor but significant amounts of other elements to impart to the alloy the chemical and physical properties required for its use in porcelain-bonded dental restorations.

Cobalt is the major component, imparting to the alloy its inherent corrosion and tarnish resistance. The chromium and molybdenum enhance this resistance; in addition they act as solid solution strengtheners and also aid in adjusting the alloy's thermal coefficient of expansion. The chromium content of the alloy is from about 25 to 30 weight percent, while that of the molybdenum is from about 5 to 7 weight percent. At lower chromium and molybdenum levels, the corrosion resistance of the alloy deteriorates considerably and the thermal coefficient of expansion becomes too high. At higher levels, the alloy becomes too hard. Preferred levels are about 28 percent chromium and 6 percent molybdenum.

Manganese and silicon, present in the alloy at levels of up to about 1.0 weight percent of each element with a minimum combined level of about 0.5 percent, act to tie up traces of oxygen and sulfur that may be present in the alloy and to improve the castability of the alloy. A combined level of much above about 2 percent, however, results in too brittle an alloy. Levels of about 0.5 percent manganese and 0.6 percent silicon are preferred. Carbon is added to the alloy at levels up to about 0.3 percent, acting as a strengthening element. Higher levels tend to produce too hard an alloy. The preferred carbon level is about 0.05 percent.

The gallium and indium, added at levels up to about 4 weight percent each, with a minimum combined level of about 1.25 percent, help to soften the alloy, regulate its thermal coefficient of expansion, and improve the bonding of the alloy to porcelain through the formation of adherent oxides. A combined level of less than about 1.25 percent is insufficient for this purpose, while individual levels of greater than about 4 percent tend to produce alloys which do not bond well to porcelain. Preferably the alloy contains gallium and indium at levels of from about 1.5 to 3 weight percent, either one to the exclusion of the other or combined.

The alloy may contain minor amounts, up to a total of 0.5 weight percent, of other nonessential ingredients such as iron and nickel, as well as trace amounts of incidental impurities, which do not deleteriously affect the basic advantageous features of the alloy obtained in accordance with the present invention.

The alloy is readily prepared either by simply combining the individual constituents in a melt or by the addition of the gallium and/or indium to a melt of a commercially available biocompatible cobalt/chromium/molybdenum alloy such as Vitallium ®, supplied by Howmedica, Inc., New York, N.Y. The cast alloy possesses the following desirable properties:
Tensile Properties (minimum)
 0.2% yield stress, psi—75,000
 Ultimate tensile strength, psi—85,000
 Elongation, %—4
Coefficient of thermal expansion (25°–650° C.), /°C.—$14.7$–$15.1 \times 10^{-6}$
Microhardness, Vickers—300–325

In addition, the alloy shows adequate corrosion resistance and readily bonds to porcelain. Suitable porcelains for bonding include, for example, Microbond ® Hi-Life ® Body Porcelain supplied by Howmedica, Inc., New York, N.Y. Casting and porcelain bonding techniques applicable to the alloy are disclosed in U.S. Pat. No. 3,948,653, which is incorporated herein by reference.

The following examples are merely illustrative and are not to be construed as limiting the invention, the scope of which is defined by the appended claims.

EXAMPLE 1

A dental alloy was prepared by melting at 2750° F. a sample of FHS Vitallium ® stock in a centrifugal induction casting machine. The desired amount of indium was then added during a single induction melting cycle and the resulting alloy melt was investment cast into a thermal expansion rod, a hardness coupon and a bend strip.

The alloy showed the following chemical analysis in weight percent:
Chromium—28.0
molybdenum—6.1
manganese—0.5
silicon—0.6
carbon—0.05
indium—1.7
cobalt—62.9

The alloy was evaluated for physical and chemical properties as follows:

Tensile Properties

The as-cast alloy was recast into specimens 40 mm long with a smooth grip diameter of 4.5 mm and gage diameter of 3 mm. An Instron tensile machine was then used to determine the 0.2 percent yield strength (YS), ultimate tensile strength (UTS) and elongation.

Microhardness

Rectangular hardness coupons (20 mm×13 mm×4 mm) were cast and cut into two pieces. One piece was mounted in bakelite with a 10 mm×13 mm surface exposed and then metallographically polished thru 600 grit silicon carbide polishing paper. Vickers microhardness of the sample was then determined using a Leitz Wetzlar microhardness tester with a 1000 gram load.

Thermal Expansion

Test samples were cast rods 0.25 inch in diameter and about 0.5 inch long with flat, parallel ends. The rods were placed vertically in a du Pont 990 Thermal Analyzer unit with auxiliary du Pont 943 Thermomechanical Analyzer (TMA) attachment, the LVDT measurement probe resting on the top flat end of the rod. The samples were tested from $-10°$ C. to $+675°$ C. using a heating rate of 10° C./min and platinum as the calibration standard, the data from 25° to 650° C. being used for comparison.

Corrosion

Both anodic polarization and crevice corrosion of the alloy were determined. With anodic polarization, the hardness coupons after testing were drilled through the back to accept an electrode and then repolished. The sample was then evaluated by potentiodynamic anodic polarization in 0.9 percent saline solution, using a Princeton Applied Research Model 173 Potentiostat and Model 175 Programmer with a scan rate of 2.0 mV/sec, from below thru the corrosion potential, with the scan terminated at a current of 100 microamps. In determining crevice corrosion, a crevice was artificially created by placing a tight-fitting teflon ring on a thermal expansion rod and the ability of the rod to recover from an imposed electrochemical attack was monitored. An overvoltage of $+1$ volt was initially applied to the sample, and the potential then lowered to allow the alloy to recover and repair itself. The overvoltage and recovery cycle was repeated at a higher potential and the process continued until the alloy no longer recovered or repassivated; the potential at this point is called the protection potential. An alloy is not susceptible to pitting or crevice corrosion if its corrosion potential is greater than its protection potential.

Bonding to Porcelain

The general procedure for porcelain application disclosed in U.S. Pat. No. 3,948,653 was followed using slurry orange A as bonding agent and Microbond ® Hi-Life ® Body Porcelain. The bonding agent firing was at 1400° to 1900° F. in vacuum, the opaque porcelain firing was at 1400° to 1800° F. in vacuum, and the body porcelain was at 1400° to 1750° F. in vacuum for a first bake, at 1400° to 1775° F. in vacuum for a second bake and at 1400° to 1800° F. in air for a third bake.

The following summarizes the evaluation of the alloy:
Tensile properties
0.2% YS, psi—85,600
UTS, psi—102,700
Elongation, %—3.8
Microhardness, Vickers—325
Coefficient of thermal expansion (25°-650° C.) /°C.—$15.0 \times 10^{-6}$
Corrosion
Corrosion potential, mV——420
Protection potential, mV——450
Porcelain bonding—very good

EXAMPLE 2

The preparation and testing of Example 1 were repeated using a direct melt at 2750° F. of the individual alloy constituents with both gallium and indium present. The alloy assayed 28.4 weight percent chromium, 6.5 percent molybdenum, 0.5 percent manganese, 0.6 percent silicon, 2.0 percent gallium and 2.8 percent indium. Testing of the alloy showed:
Tensile properties
0.2% YS, psi—73,900
UTS, psi—82,300
Elongation, %—4
Microhardness, Vickers—275
Coefficient of thermal expansion (25°-650° C.) /°C.—$14.3 \times 10^{-6}$
Corrosion
Corrosion potential, mV——408
Protection potential, mV——+100
Porcelain bonding—good

EXAMPLE 3

The preparation and testing of Example 1 were repeated using an FHS Vitallium melt and gallium rather than indium addition to give an alloy assaying 25.1 weight percent chromium, 5.7 percent molybdenum and 2.95 percent gallium with the following properties:
Tensile properties
0.2% YS, psi—73,700
UTS, psi—113,500
Elongation, %—13.6
Microhardness, Vickers—318
Coefficient of thermal expansion (25°-650° C.) /°C.—$15.0 \times 10^{-6}$
Porcelain bonding—good
I claim:

1. A nonprecious dental alloy consisting essentially of the following constituents in approximate percentage by weight:

chromium—25–30
molybdenum—5–7
manganese—0–1.0
silicon—0–1.0
carbon—0–0.3
gallium—1.5–3
indium—1.5–3
cobalt—balance said constituents accounting for at least 99.5 weight percent of the alloy, the sum of the manganese and the silicon being at least about 0.5 percent.

2. The dental alloy of claim 1 containing about 28 percent chromium and about 6 percent molybdenum.